United States Patent [19]
Bond et al.

[11] Patent Number: 5,827,513
[45] Date of Patent: Oct. 27, 1998

[54] METHODS OF TREATING INSULIN-DEPENDENT DIABETES MELLITUS BY ADMINISTRATION OF IL-10

[75] Inventors: Martha W. Bond; Kevin W. Moore, both of Palo Alto, Calif.; Kenneth Pennline, Landing, N.J.; Paulo J. M. Vieira, Palo Alto, Calif.

[73] Assignee: Schering Corporation, Kenilworth, N.J.

[21] Appl. No.: 406,929

[22] PCT Filed: Sep. 28, 1993

[86] PCT No.: PCT/US93/09030

§ 371 Date: Mar. 30, 1995

§ 102(e) Date: Mar. 30, 1995

[87] PCT Pub. No.: WO94/08606

PCT Pub. Date: Apr. 28, 1994

Related U.S. Application Data

[63] Continuation of Ser. No. 955,523, Oct. 1, 1992, abandoned, which is a continuation-in-part of Ser. No. 904,124, Jun. 25, 1992, abandoned, which is a division of Ser. No. 546,235, Aug. 6, 1990, abandoned.

[51] Int. Cl.$^6$ ............................. A61K 38/20; C07K 14/54
[52] U.S. Cl. ......................... 424/85.2; 530/351; 514/866
[58] Field of Search ....................... 435/69.52; 424/85.2; 530/351; 514/12

[56] References Cited

FOREIGN PATENT DOCUMENTS

0405980 A1  1/1991  European Pat. Off. .

OTHER PUBLICATIONS

Cohen, J. Science 270:908, 1995.
Pankewycz et al. Eur. J. Immunol 22: 2017–2023, 1992.
Sarvetnick et al. Ped. Res. 33: 51, 1993.
Wogensen et al. J. Exp. Med 179: 1379–1384, 1994.
Lee et al. J. Clin. Invest. 93: 1332–1338, 1994.
Moritani et al. Intern. Immunol. 6: 1927–1936, 1994.
Moratini et al., 1996, *J. Clin. Invest.* 98(8):1851–1859.
Pennline et al., 1994, *Clinical Immunology and Immunopathology* 71(2):169–175.

*Primary Examiner*—John Ulm
*Assistant Examiner*—Christine Saoud
*Attorney, Agent, or Firm*—Norman C. Dulak; Cynthia L. Foulke

[57] ABSTRACT

Disclosed is a method for treating an individual who is predisposed to develop insulin-dependent diabetes mellitus. To practice the method, an amount of interleukin-10 protein effective to maintain blood glucose levels at a non-diabetic level is administered to an individual predisposed to develop the disease.

5 Claims, 2 Drawing Sheets

METHODS OF TREATING INSULIN-DEPENDENT DIABETES MELLITUS BY ADMINISTRATION OF IL-10

This is the United States National Application corresponding to International Application No. PCT/US93/09030 and designating the United States, which PCT application in turn is a Continuation of U.S. Ser. No. 07/955,523, filed Oct. 1, 1992, now abandoned; which is a Continuation-In-Part of U.S. Ser. No. 07/904,124, filed Jun. 25, 1992, now abandoned; which is a Divisional of U.S. Ser. No. 07/546,235, filed Aug. 6, 1990, now abandoned.

This invention relates to the use of interleukin-10 (IL-10), formerly known as cytokine synthesis inhibitory factor (CSIF), for the treatment or prevention of insulin-dependent (type 1) diabetes mellitus.

BACKGROUND OF THE INVENTION

Immune responses to an antigen are classified as being predominantly either cell-mediated, exemplified by the phenomenon of delayed-type hypersensitivity (DTH), or humoral, exemplified by the production of antibodies. Cell-mediated immunity is of paramount importance for the rejection of tumors and for recovery from many viral, bacterial, protozoan and fungal infections. In contrast, a humoral immune response is the most effective form of immunity for eliminating toxins and invading organisms from circulation.

It has been observed that for different antigens one or the other of these two responses often predominates in a mutually exclusive fashion, and that the severity of some diseases, e.g., leprosy, leishmaniasis, and some types of autoimmunity, may be due the inappropriate dominance of one class of response over the other [Mosmann et al., Immunol. Today 8:223–227 (1987); Mosmann et al., Ann. Rev. Immunol. 7:145–173 (1989); Parish, Transplant. Rev. 13:35–66 (1972); Liew, Immunol. Today 10:40–45 (1989)].

It has further been observed that sets of cytokines are separately associated with DTH reactions and humoral immune responses [Cher et al., J. Immunol. 138:3688–3694 (1987); Mosmann et al. 1987 and 1989, supra], and it is thought that diseases associated with these classes of response are caused by the inappropriate production of the associated sets of cytokines.

For example, a large body of evidence suggests that excessive production of gamma interferon (IFN-γ) is responsible for major histocompatibility complex (MHC) associated autoimmune diseases [Hooks et al., N. Eng. J. Med. 301:5–8 (1979) (elevated serum levels of IFN-γ correlated with autoimmunity); Basham et al., J. Immunol. 130:14921494 (1983) (IFN-γ can increase MHC gene product expression); Battazzo et al., Lancet, pgs. 1115–1119 (Nov. 12, 1983) (aberrant MHC gene product expression correlated with some forms of autoimmunity); Hooks et al., Ann, N.Y. Acad. Sci., Vol. , pgs. 21–32 (1980) (higher IFN-γ levels correlated to greater severity of disease in SLE patients, and histamine-release enhancing activity of interferon can be inhibited by antiinterferon sera); Iwatani et al., J. Clin. Endocrin. Metabol. 63:695–708 (1986) (anti-IFN-γ monoclonal antibody eliminated the ability of leucoagglutinin-stimulated T cells to induce HLA-DR expression)]. It is hypothesized that excess IFN-γ causes the inappropriate expression of MHC gene products which, in turn, causes autoimmune reactions against the tissues whose cells are inappropriately expressing the MHC products and displaying autoantigens in the context of the products.

Insulin-dependent diabetes mellitus (IDDM), also known as juvenile or type 1 diabetes, is an autoimmune disorder characterized by cellular infiltration (insulitis) of the pancreatic islets of Langerhans (pancreatic β cells). It is believed that IDDM is the result of cell-mediated autoimmune processes and is restricted to particular Class II HLA types.

The non-obese diabetic (NOD) mouse is also known to develop IDDM. Spontaneous IDDM occurs with an incidence of 70–90% in female NOD mice at 18–25 weeks of age. Because this disease exhibits all of the pathological and autoimmune manifestations of the human disease, NOD mice serve as an excellent model for the identification of agents that might prevent IDDM or ameliorate the effects of the disease.

In humans, development of IDDM can be conceptually divided into stages, beginning with a human leukocyte antigen (HLA)-restricted genetic susceptibility. In some genetically susceptible individuals, a triggering event activates both cellular and humoral autoimmunity.

Glucose-stimulated insulin secretion and β cell mass diminish as anti-islet autoimmunity progresses. This process culminates in overt diabetes when only residual β cell mass (estimated at <10%) remains. Complete β cell destruction typically follows within months to years of diagnosis.

Most current efforts to treat IDDM involve the use of broad immunosuppressive therapeutic agents such as azathioprine. prednisone and cyclosporin. Such agents, however, can cause damage to liver, kidney and other organs and have the undesirable effect of impairing immune protection against infection and other diseases.

In view of the above, it would be advantageous to have available agents and methods that could shift the dominance of one class of immune response to the other and, in particular, that could suppress or increase the synthesis of IFN-γ and/or other cytokines, respectively, as required for therapy. Such agents and methods would be highly advantageous for treatment of diseases associated with inappropriate or inadequate immune responses, such as tissue rejection; leishmaniasis and other parasitic diseases; and MHC-associated immune disorders including rheumatoid arthritis, systemic lupus erythematosus (SLE), myasthenia gravis, insulin-dependent diabetes mellitus and thyroiditis.

More particularly, there is a need for less toxic and more specific immunosuppressive agents which are effective in the treatment of IDDM but do not exhibit the undesirable effects of the agents used now.

SUMMARY OF THE INVENTION

The present invention fills this need by providing methods for treating an individual afflicted with or predisposed to develop an MHC-linked, cell-mediated immune disorder. More particularly, this invention provides methods for treating or preventing insulin-dependent diabetes mellitus comprising administering an effective amount of IL-10 to an individual afflicted with or predisposed to develop insulin-dependent diabetes mellitus.

In a preferred embodiment, the IL-10 is recombinant human IL-10 and is administered parenterally.

BRIEF DESCRIPTION OF THE FIGURES

This invention can be more readily understood by reference to the Description and Example below, and to the accompanying Figures, in which.

DESCRIPTION OF THE INVENTION

Figure 1:
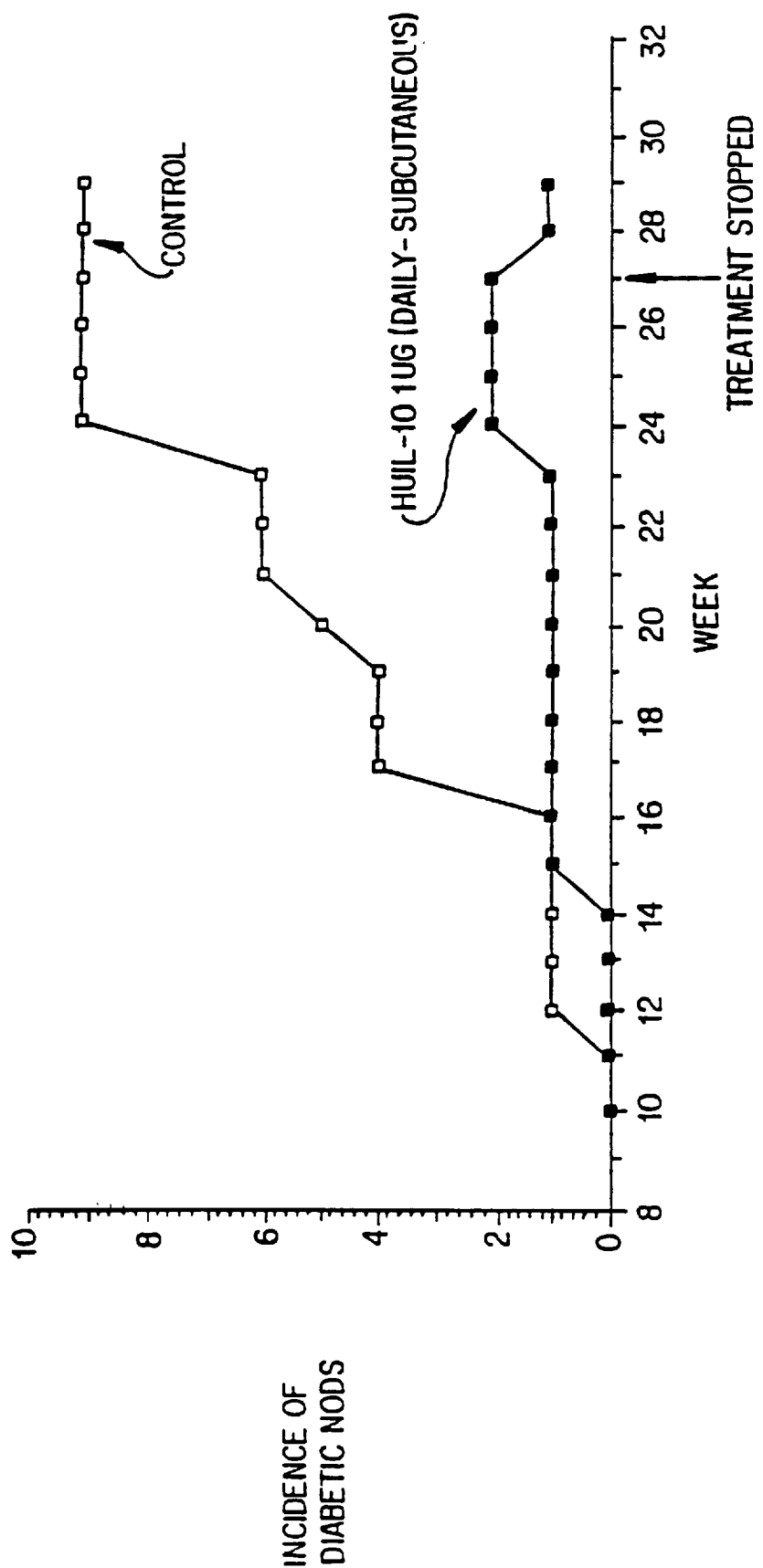
FIG. 1 is a graphical representation of the effect of recombinant human IL-10 on the incidence of diabetes in the NOD mouse, showing the incidence of the disease as a function of time.

All references cited herein are hereby incorporated in their entirety by reference.

As used herein, "interleukin-10" or "IL-10" is defined as a protein which (a) has an amino acid sequence substantially identical to a known sequence of mature (i.e., lacking a secretory leader sequence) IL-10 as disclosed in U.S. patent application Ser. No. 07/917,806, filed Jul. 20, 1992, which corresponds to International Application No. PCT/US 90/03554, Publication No. WO 91/00349, and (b) has biological activity that is common to native IL-10. For the purposes of this invention, both glycosylated (e.g., produced in eukaryotic cells such as CHO cells) and unglycosylated (e.g., chemically synthesized or produced in E. coli) IL-10 are equivalent and can be used interchangeably. Also included are muteins and other analogs, including the BCRFI (Epstein Bar Virus viral IL-10) protein, which retain the biological activity of IL-10.

IL-10 suitable for use in the invention can be obtained from a number of sources. For example, it can be isolated from culture media of activated T-cells capable of secreting the protein. Additionally, the IL-10 or active fragments thereof can be chemically synthesized using standard techniques as known in the art. See, e.g., Merrifield, Science 233:341–47 (1986) and Atherton et al., Solid Phase Peptide Synthesis. A Practical Approach, 1989, I.R.L. Press, Oxford.

Preferably, the protein or polypeptide is obtained by recombinant techniques using isolated nucleic acids encoding the IL-10 polypeptide. General methods of molecular biology are described, e.g., by Sambrook, et al., Molecular Cloning, A Laboratory Manual, Cold Spring Harbor Publish., Cold Spring Harbor, N.Y., 2d ed. 1989 and by Ausubel et al. (eds.) Current Protocols in Molecular Biology, Green/Wiley, N.Y. (1987 and periodic supplements). The appropriate sequences can be obtained using standard techniques from either genomic or cDNA libraries. Polymerase chain reaction (PCR) techniques can be used. See, e.g., PCR Protocols: A Guide to Methods and Applications, 1990, Innis et al. (Ed.), Academic Press, New York, N.Y.

Libraries are constructed from nucleic acid extracted from appropriate cells. See, for example, International Application Publication No. WO 9100349, which discloses recombinant methods to make IL-10. Useful gene sequences can be found, e.g., in various sequence databases, e.g., Gen Bank and EMBL for nucleic acid, and PIR and Swiss-Prot for protein, c/o Intelligenetics, Mountain View, Calif.; or the Genetics Computer Group, University of Wisconsin Biotechnology Center, Madison, Wis.

Clones comprising sequences that encode human IL-10 have been deposited with the American Type Culture Collection (ATCC), Rockville, Md., under Accession Numbers 68191 and 68192. Identification of other clones harboring the sequences encoding IL-10 is performed by either nucleic acid hybridization or immunological detection of the encoded protein, if an expression vector is used. Oligonucleotide probes based on the deposited sequences disclosed in International Application Publication No. WO 9100349 are particularly useful. Oligonucleotide probes useful for identification of the sequences can also be prepared from conserved regions of related genes in other species. Alternatively, degenerate probes based on the amino acid sequence of IL-10 can be used.

Standard transfection methods can be used to produce prokaryotic, mammalian, yeast or insect cell lines which express large quantities of the polypeptide. Exemplary E. coli strains suitable for both expression and cloning include W3110 (ATCC No. 27325), JA221, C600, ED767, DH1, LE392, HB101, X1776 (ATCC No. 31244), X2282, RR1 (ATCC No. 31343). Exemplary mammalian cell lines include COS-7 cells, mouse L cells and CHO cells. See Sambrook (1989) and Ausubel et al. (1987 and supplements).

Various expression vectors can be used to express DNA encoding IL-10. Conventional vectors used for expression of recombinant proteins in prokaryotic or eukaryotic cells may be used. Preferred vectors include the pcD vectors described by Okayama et al., Mol. Cell. Biol. 3:280–289 (1983); and Takebe et al., Mol. Cell. Biol. 8:466–472 (1988). Other SV40-based mammalian expression vectors include those disclosed in Kaufman et al., Mol. Cell. Biol. 2:1304–1319 (1982) and U.S. Pat. No. 4,675,285. These SV40-based vectors are particularly useful in COS7 monkey cells (ATCC No. CRL 1651), as well as in other mammalian cells such as mouse L cells. See also, Pouwels et al. (1989 and supplements) Cloning Vectors: A Laboratory Manual, Elsevier, N.Y.

The IL-10 may be produced in soluble form such as a secreted product of transformed or transfected yeast or mammalian cells. The peptides can then be purified by standard procedures that are well known in the art. For example, purification steps could include ammonium sulfate precipitation, ion exchange chromatography, gel filtration, electrophoresis, affinity chromatography and the like. See, e.g., Jakoby (ed.), Enzyme Purification and Related Techniques. Methods in Enzymology 22:233–577 (1977) and Scopes, R., Protein Purification Principles and Practice (Springer-Verlag, New York, 1982).

Alternatively, IL-10 may be produced in insoluble form such as aggregates or inclusion bodies. The IL-10 in such a form is purified by standard procedures that are well known in the art. Examples of purification steps include separating the inclusion bodies from disrupted host cells by centrifugation, solubilizing the inclusion bodies with chaotropic agents and reducing agents, diluting the solubilized mixture, and lowering the concentration of chaotropic agent and reducing agent so that the peptide assumes a biologically active conformation. For specifics of these procedures, see, e.g., Winkler et al., Biochemistry 25:4041–4045 (1986); Winkler et al., Biotechnology 3:992–998 (1985); Koths et al,. U.S. Pat. No. 4,569,790.

The nucleotide sequences used to transfect the host cells can be modified according to standard techniques to yield IL-10 or fragments thereof with a variety of desired properties. Such modified IL-10 can vary from the naturally-occurring sequence at the primary structure level, e.g., by amino acid, insertions, substitutions, deletions and fusions. These modifications can be used in a number of combinations to produce the final modified protein chain.

The amino acid sequence variants can be prepared with various objectives in mind, including increasing serum half life, facilitating purification or preparation, improving therapeutic efficacy, and lessening the severity or occurrence of side effects during therapeutic use. The amino acid sequence variants are usually predetermined variants not found in nature, although others may be post-translational variants, e.g., glycosylation variants or proteins which are conjugated to polyethylene glycol (PEG), etc. Such variants can be used in this invention as long as they retain the biological activity of IL-10.

Modifications of the sequences encoding the polypeptides may be readily accomplished by a variety of techniques, such as site-directed mutagenesis [Gillman et al., Gene 8:81–97 (1979); Roberts et al., Nature 328:731–734 (1987)]. Most modifications are evaluated by routine screening in a suitable assay for the desired characteristic. For instance, International Application Publication No. WO 91/00349 describes a number of in vitro assays suitable for measuring IL-10 activity.

Preferably, human IL-10 is used for the treatment of humans, although viral or mouse IL-10, or IL-10 from some other mammalian species, could be used instead. Most preferably, the IL-10 used is recombinant human IL-10. The preparation of human and mouse IL-10 has been described in International Application Publication No. WO 91/00349. The cloning and expression of a viral IL-10 (BCRFI protein) from Epstein Bar virus has been disclosed by Moore et al. [Science 248:1230 (1990)].

Recombinant human IL-10 is also an article of commerce, available for purchase, e.g., from PeproTech, Inc., Rocky Hill, N.J.

Individuals suitable for treatment by the methods of this invention include any individual at risk (predisposed) for developing the clinical symptoms of IDDM. In most cases such individuals will be young females, although males may also be predisposed to develop the disease. Because β islet cell damage has usually occurred by the time clinical manifestations of IDDM are evident, it is preferable that treatment be instituted before that point. It may also be possible to treat individuals afflicted with clinical IDDM, however, if the destruction of the islet cells is not too extensive at the time treatment is initiated.

Due to the genetic basis of IDDM, individuals suspected to be at risk of developing the disease can often be identified through reviews of family histories. More definitive identification of individuals at risk can be made by screening for any of the well known markers having sufficient specificity to be predictive for the development of IDDM. Such markers include but are not limited to cytoplasmic islet cell antibodies (ICA), insulin autoantibodies (IAA) and diminished first-phase insulin secretion in response to an intravenous glucose load (IVGTT). A review of such markers has been published by Wilson et al. [Ann. Rev. Med. 41:497–508 (1990)].

Cytoplasmic islet cell antibodies are autoantibodies of the immunoglobulin G (IgG) subclass which can be detected by specific binding to frozen sections of human and animal pancreas [Colman et al., Diabetes Care 11:367–368 (1988)]. ICA positivity has been shown to have a positive predictive value by life table analysis of 80% at nine years of follow-up [Dib et al., Br, Med. J. 292:1670 (1986)].

Antibodies against insulin (IAA) can often be detected in diabetics at the time IDDM is diagnosed and in some first-degree relatives by using fluid-phase radioimmunoassays with $^{125}$I-insulin as described by Vardi et al. [Diabetes 36:1286–1291 (1987)] and Srikanta et al. [Diabetes 35:139–142 (1986)]. It is believed that the concentration of IAA reflects the rate of autoimmune destruction, and that infants with high IAA levels show a more rapid progression of the disease.

Diminished first-phase insulin secretion is believed to be a measure of the degree of β cell destruction [Ganda et al., Diabetes 33:516–521 (1984)]. In one study, an IVGTT test less than the first percentile carried a relative risk for progressing to diabetes of 79. By using variables from this study, Jackson et al. [Clin. Res. 36:588A (1988)] have developed a dual-parameter model to estimate the time to onset of overt diabetes.

As used herein, the term "effective amount" means an amount of IL-10 sufficient to ameliorate (reduce) one or more of the markers predictive of development of IDDM or one or more of the well known symptoms of IDDM, as determined. e.g., by glucose tolerance tests [Klimt et al., Diabetes 18:299 (1969)] or measurement of the levels of blood glucose [Jarret et al., Lancet 2:1009 (1976)], ketone bodies [National Diabetes Group, Diabetes 28:1039 (1979)], blood insulin [Soeldner et al., Diabetes 14:771 (1965)] or anti-islet cell antibodies [Lernmark et al., N. Eng. J. Med. 299:375 (1978)].

Generally, IL-10 is administered as a pharmaceutical composition comprising an effective amount of IL-10 and a pharmaceutical carrier. A pharmaceutical carrier can be any compatible, non-toxic substance suitable for delivering the compositions of the invention to a patient.

Administration is preferably parenteral by intraperitoneal, intravenous, subcutaneous or intramuscular injection or infusion or by any other acceptable systemic method. Administration by intramuscular or subcutaneous injection is most preferred. Alternatively, the IL-10 may be administered by an implantable or injectable drug delivery system [see, e.g., Urquhart et al., Ann. Rev. Pharmacol. Toxicol. 24:199 (1984); Lewis, Ed., *Controlled Release of Pesticides and Pharmaceuticals,* 1981, Plenum Press, New York, N.Y.; U.S. Pat. Nos. 3,773,919 and 3,270,960]. Oral administration may also be carried out, using well known formulations which protect the IL-10 from gastrointestinal proteases.

Compositions useful for parenteral administration of such drugs are well known [see, e.g., Remington's Pharmaceutical Science, 18th Ed. (Mack Publishing Company, Easton, Pa. 1990)]. When administered parenterally, the IL-10 is formulated in a unit dosage injectable form (solution, suspension, emulsion) in association with a pharmaceutical carrier. Examples of such carriers are normal saline, Ringer's solution, dextrose solution, and Hank's solution. Non aqueous carriers such as fixed oils and ethyl oleate may also be used. A preferred carrier is 5% dextrose/saline. The carrier may contain minor amounts of additives such as substances that enhance isotonicity and chemical stability, e.g., buffers and preservatives. The IL-10 is preferably formulated in purified form substantially free of aggregates and other source proteins at a concentration in the range of about 5 to 20 μg/ml. Any of the well known carrier proteins such as human serum albumin can also be added if desired.

IL-10 can also be delivered by standard gene therapy techniques, including, e.g., direct DNA injection into tissues, the use of recombinant viral vectors and implantation of transfected cells. See, e.g., Rosenberg, J. Clin. Oncol. 10:180 (1992).

IL-10 can be administered alone or in combination with one or more of the other agents commonly used to treat or ameliorate the symptoms of IDDM. For example, drugs such as insulin, cyclosporin, prednisone or azathioprine can be administered with the IL-10. Because of the activity of the IL-10, other immunosuppressive drugs can be used in lower amounts, thereby reducing the serious side-effects normally associated with the use of such drugs.

Other cytokine agonists or antagonists that augment the activity of IL-10 can also be administered in combination with the IL-10. For example, IL-10 is believed to exert its anti-diabetic effects at least in part by inhibiting TH1 cell activity and promoting TH2 cell activity. TH1 cells potentiate cellular immune activity and are likely to be responsible for controlling the cellular autoimmune processes involved in islet cell destruction. TH2 cells are involved in the humoral response. The net effect of the IL-10 is thus a shift in the immune response away from the cellular autoimmune destruction of the islet cells. IL-4 and IL-10 act together to promote TH2 immunity.

Co-administration of one or more other agents can be concomitant (together with the administration of the IL-10) or sequential (before or after the administration of the IL-10). All of the administered agents should be present in the patient at sufficient levels to be therapeutically effective. Typically, if a second agent is administered within about the half-life of the first agent, the two agents are considered to be co-administered.

The effective dose of IL-10 may range from about 1 ng to about 100 mg per kg of body weight per day. Typically, the dose will range from about 0.1 to 1,000 µg of IL-10 per kg of body weight per day. The effective amount for a particular patient will vary depending on factors such as the severity of the IDDM being treated, the overall health and age of the patient, the method of administration and the severity of any observed side-effects.

EXAMPLE

The following non-limiting Example will serve to illustrate the present invention.

To determine the effect of IL-10 on the development of IDDM, ten 10-week-old female NOD mice (Taconic Farms, Inc. Germantown, N.Y.) were injected subcutaneously with 1 µg of recombinant human IL-10 produced in Chinese hamster ovary (CHO) cells and purified by standard methods. These injections were made daily, until the animals were 27 weeks old. A group of control animals was similarly injected, except that mouse serum albumin was used instead of IL-10.

Tail vein bleeds were performed weekly to determine the blood glucose levels (BGL) and the incidence of diabetes. The animals were fed normal lab chow (Purina Pico Lab Rodent Chow) ad libitum and injected in the afternoon. BGL readings were obtained on the non-fasted animals in the morning hours by absorbing blood drops from the tail vein bleeds on glucose test strips and then reading the results in a GLUCOSCAN 3000 blood glucose meter (Lifescan Inc., Mountain View, Calif.). Animals with BGL values above 200 mg/dl were considered to be diabetic. The results are shown in FIGS. 1 and 2.

As shown in FIG. 1, where the number of diabetic animals is represented as a function of time, the administration of IL-10 (lower curve) significantly reduced the incidence of diabetes; only 1 of the 10 animals showed a BGL sufficiently high to be classified as diabetic. In contrast, 9 of the 10 control animals (upper curve) were so classified.

Figure 2:
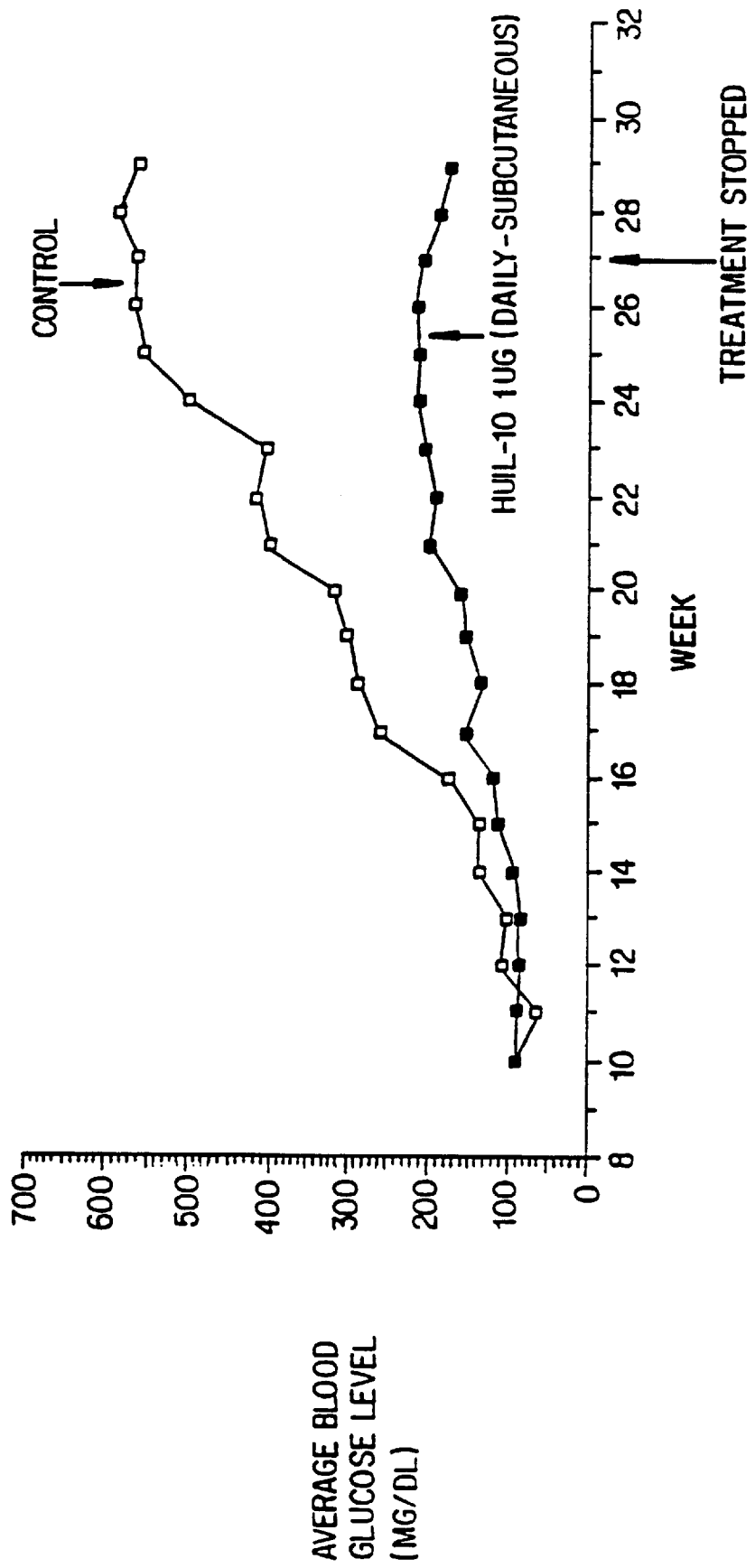
FIG. 2 is a graphical representation of the effect of recombinant human IL-10 on average glucose levels in NOD mice, showing the glucose levels as a function of time.

In FIG. 2, where average BGL is shown as a function of time, it can be seen that the average BGL of the control group was 575 mg/dl, while the average for the IL-10-treated animals was less than 200 mg/dl at the 29-week time point.

It is thus clear from FIGS. 1 and 2 that the administration of the IL-10 prevented the development of diabetes in the NOD mice. The mechanism(s) by which IL-10 produced this result is unknown but is in any event not essential to the practice of this invention.

Many modifications and variations of this invention can be made without departing from its spirit and scope, as will become apparent to those skilled in the art. The specific embodiments described herein are offered by way of example only, and the invention is to be limited only by the terms of the appended claims.

What is claimed is:

1. A method of treating an individual who is predisposed to develop insulin-dependent diabetes mellitus comprising administering IL-10 protein in an amount effective to maintain blood glucose levels at a non-diabetic level.

2. The method of claim 1 in which the IL-10 is human IL-10.

3. The method of claim 2 in which the IL-10 is recombinant human IL- 10.

4. The method of claim 1 in which the administration is parenteral.

5. The method of claim 4 in which the parenteral administration is by intramuscular or subcutaneous injection.

* * * * *